United States Patent [19]

Forse et al.

[11] Patent Number: 5,260,336
[45] Date of Patent: Nov. 9, 1993

[54] MONOUNSATURATED FAT AS DIETARY SUPPLEMENT TO MINIMIZE THE EFFECTS OF CATABOLIC ILLNESS

[75] Inventors: R. Armour Forse, Brookline; Edward A. Mascioli, Needham, both of Mass.

[73] Assignee: New England Deaconess Hospital Corporation, Boston, Mass.

[21] Appl. No.: 876,189

[22] Filed: Apr. 30, 1992

[51] Int. Cl.⁵ .................. A61K 31/20; A61K 31/22
[52] U.S. Cl. ........................ 514/560; 514/549
[58] Field of Search ............. 514/549, 560, 552

[56] References Cited

U.S. PATENT DOCUMENTS

| | | | |
|---|---|---|---|
| 4,196,218 | 4/1980 | Thiele | 514/560 |
| 4,528,197 | 7/1985 | Blackburn | 514/560 |
| 4,752,618 | 6/1988 | Mascioli et al. | 514/549 |
| 4,820,731 | 4/1989 | Mascioli et al. | 514/549 |
| 4,847,296 | 7/1989 | Babayan et al. | 514/552 |
| 4,921,877 | 5/1990 | Cashmere et al. | 514/549 |
| 5,085,883 | 2/1992 | Garleb et al. | 514/53 |

FOREIGN PATENT DOCUMENTS 0304354 7/1987 European Pat. Off. .
0302769 2/1989 European Pat. Off. .

OTHER PUBLICATIONS

Martindale, The Extra Pharmacopoeia (1982) 28th edition, p. 697.
Replete (Clintec Nutrution Company, 1992).
Sagher, F. A. et al., *J. Pediatr. Gastroenterol. Nutr.* 13: 83–89 (1991).
Inmunonutril (Clinical Nutrition, Jul. 26, 1991).
Promote (Ross Laboratories, Sep. 1991).
Immun-AID (Kendall McGaw Laboratories, Inc., 1990).
Mensick, R. P. et al., *Metabolism* 38(2): 172–178 (Feb. 1989).
Kelley, V. E. et al., *Transplantation* 48(1): 98–102 (Jul. 1989).

*Primary Examiner*—Frederick E. Waddell
*Assistant Examiner*—Raymond J. Henley, III

[57] ABSTRACT

Disclosed is a method of minimizing the effects of a catabolic illness in an individual by administering to the individual a diet which is controlled in the type of fatty acid intake. The diet comprises an oil rich in $\omega 9$ monounsaturated fatty acids, preferably oleic acid. Oils rich in monounsaturated fatty acids include olive oil, canola oil and high oleic acid safflower or high oleic acid sunflower oil. The diet can also be administered to an individual to minimize infection or to minimize the risk of infection in the individual. A dietary supplement useful in methods of the invention and a structured lipid are also disclosed.

24 Claims, No Drawings

MONOUNSATURATED FAT AS DIETARY SUPPLEMENT TO MINIMIZE THE EFFECTS OF CATABOLIC ILLNESS

BACKGROUND OF THE INVENTION

Under normal nutritional and physiological conditions, fuel requirements of the body are met primarily by glucose and fatty acid metabolism. However, during abnormal metabolic stress states induced by trauma or sepsis, one of the effects is a decrease of fat and glucose utilization. Under these conditions, a high rate of bodily protein catabolism occurs. This metabolic response results in the acceleration of protein degradation and an elevation of energy expenditure, or hypercatabolism. Bodily protein catabolism provides the precursors for oxidation of branched chain amino acids and the synthesis and release of alanine for hepatic metabolism as a gluconeogenic substrate. Urinary nitrogen excretion is often elevated and the individual suffers a negative nitrogen balance. If the stress is persistent, the nitrogen losses will eventually deplete the individual's protein stores resulting in a progressive deterioration of lean body mass and multiple organ failure.

Stress of injury in an individual, such as trauma or sepsis, is often accompanied by total or partial dysfunction of the gastro-intestinal tract. These individuals are often hospitalized and must receive most or all of their daily nutritional requirements parenterally and/or enterally in order to sustain protein synthesis and avoid malnutrition. For example, many patients are administered total parenteral nutrition which includes a source of fatty acids. Standard parenteral nutrition diets have long chain fatty acid triglyceride (LCT) emulsions, composed of either soybean or safflower oil, as the primary lipid source. These oils are high in $\omega 6$ fatty acids, particularly linoleic acid.

As an alternative or additive fatty acid source, medium chain triglycerides (MCT) formed from saturated fatty acids with 6-12 carbon backbones have been used in various formulations. MCTs are metabolized more rapidly than long chain triglycerides in that they enter the body through the portal rather than lymphatic pathway. Metabolic products of MCT do not require carnitine to enter into the mitochondria where they undergo $\beta$-oxidation.

One current high protein enteral liquid nutrition supplement, REPLETE TM (Clintec Nutrition Company), provides MCTs to minimize diarrhea caused by fat intolerance. Another formulation for enteral feedings, IMMUN-AID TM (Kendall McGaw Laboratories, Inc.), includes both MCTs and canola oil as sources of fat and is reported to improve immune function in an immunocompromised, stressed patient. Canola oil is discussed in the IMMUN-AID TM literature as being included in the composition as a source of $\omega 3$ fatty acids, which are reported to improve the cell-mediated immune response in animal models.

Canola oil not only provides $\omega$-3 fatty acids; it and olive oil are the richest natural sources of monounsaturated fatty acids. Another new enteral product, PROMOTE TM (Ross Laboratories), uses high oleic acid safflower oil, canola oil and MCT's as lipid sources. The primary monounsaturated fatty acid in canola oil, olive oil, and high oleic acid safflower oil is oleic acid, an $\omega 9$ monounsaturated fatty acid. Monounsaturated oils are not appreciably elongated to a 20-carbon fatty acid. Thus, unlike oils high in polyunsaturated fatty acids, such as $\omega 3$ and $\omega 6$ fatty acids, administration of monounsaturated oils can not act as substrate in the prostanoid synthesis pathway which forms prostaglandins from fatty acids. Since the amount of certain prostaglandins in the system, particularly elevated levels of the "2" series prostaglandins, have been shown to be related to deleterious response to endotoxin in animal studies, reducing primarily with oils has positive health effects.

Accordingly, an object of the invention is to provide a method of treating patients having metabolic stress or sepsis using a diet which includes modifications in fatty acid content.

Another object of the invention is to provide an enteral or parenteral solution which can assist a patient combat challenge by metabolic stress or sepsis.

A further object of the invention is to provide an enteral or parenteral diet having reduced polyunsaturated fat content without the problems caused by high levels of MCT'S.

These and other objects and features of the invention will be apparent from the detailed description.

SUMMARY OF THE INVENTION

The present invention features a method of minimizing the effects of catabolic illness or response to sepsis in an individual. The method comprises administering a diet, preferably a parenteral diet, which is controlled in the type of fatty acid intake to the individual. The diet of the present invention includes an oil having an $\omega 9$ monounsaturated fatty acid as its major fatty acid component as the primary lipid source. The preferred $\omega 9$ monounsaturated fatty acid is oleic acid. Oils rich (about 45-85%) in oleic acid include olive oil, canola oil and high oleic acid safflower or high oleic acid sunflower oil.

Individuals to be treated using this high monounsaturated fat diet are catabolic for a variety of reasons; for example, the catabolism may be due to surgery, burns, trauma or inflammatory process or the individuals may have an infection at the time of administration of the diet or may be at high risk of infection due to some immunocompromise. Individuals at risk of infection include those suffering with secondary immunosuppression due to chemotherapy or diabetes mellitus, protein-malnourished patients, or patients undergoing surgery, e.g., abdominal or thoracic surgery. While the oil rich in monounsaturated fatty acids can be administered enterally or parenterally, parenteral administration is preferable because of better absorption by the body. Often patients in stressed states have difficulty absorbing any food, let alone long chain fatty acids. The $\omega 9$ monounsaturated fatty acids can constitute 15-85% of the total fatty acids in diet, providing 5-75% of the total calories.

The $\omega 9$ monounsaturated fats can be given in a variety of ways. For example, the diet could include just the high oleic acid oils or there could be a physical mixture of the $\omega 9$ monounsaturated fat containing oils with other fat sources, such as medium chain triglycerides or fish oils. These other oils may be necessary to provide essential fatty acids. In the alternative, the $\omega 9$ monounsaturated oils could be administered as part of a structured lipid. This structured lipid could have the form:

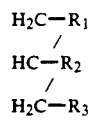

where at least one of the $R_1$, $R_2$ and $R_3$ is an monounsaturated fat, and the others of $R_1$, $R_2$ and $R_3$ are selected from the group consisting of $C_6$-$C_{12}$ saturated fats, $C_{14}$-$C_{20}$ primarily unsaturated fats, and mixtures thereof. Preferred structured lipids would contain one $C_6$-$C_{12}$ fat, one $\omega 9$ monounsaturated fat (e.g., oleic acid), and one $C_{14}$-$C_{20}$ unsaturated fat (e.g., linoleic or linolenic acid).

The invention also features a dietary supplement, preferably a parenteral dietary supplement, having 10 to 90 percent by weight of an oil having an $\omega 9$ monounsaturated fatty acid as the major fatty acid component, 1-2 percent by weight of an emulsifier and sterile water. The dietary supplement may also include an osmolality modifier and other essential nutrients. The dietary supplement can be administered to an individual to minimize the effects of a catabolic illness or an infection in the individual or to minimize the risk of infection in the individual.

DETAILED DESCRIPTION OF THE INVENTION

The present invention relates to a method, diet, and dietary supplement to minimize the effects of catabolic illness. The method utilizes dietary control of the type of fatty acids provided to an individual experiencing catabolic stress following surgery, trauma or burn injury. A diet useful in the method includes as the primary lipid source an oil having a monounsaturated fatty acid as the major fatty acid component is administered to the individual. Although the diet can be administered enterally, parenteral administration is preferred. Olive oil and canola oil, which have oleic acid, a monounsaturated fatty acid, as the major fatty acid component, are preferred sources of the oil for administration to a stressed individual. The diet provides improved support of the individual's physiology during a catabolic illness (e.g., decreased metabolic acidosis, decreased hypotension, and improved maintenance of metabolic rate). Individuals to be treated may be catabolic due to trauma, burn, AIDS, sepsis, cancer or surgery.

A diet including an oil having an $\omega 9$ monounsaturated fatty acid as the major fatty acid component can also be administered to an individual to minimize the effects of infection in the individual or to minimize the risk of subsequent infection in an individual at risk of infection. Individuals at risk of infection include those suffering with secondary immunosuppression due to chemotherapy or diabetes mellitus, protein-malnourished individuals, or individuals undergoing abdominal surgery. The infections can be wound infections, empyemas, bacteremias, abscesses, or septicemias. These infections are caused by a variety of infectious agents including bacteria (e.g., *E. coli*, Pseudomonas, Klebsiella, *Staphylococcus aureus* or *albus*), viruses (e.g., *Herpes simplex* or *zoster*), parasites, and fungi (e.g., Candida).

Conventional dietary supplements have primarily soybean or safflower oil as their lipid or fatty acid source. By replacing these predominantly $\omega 6$ fatty acid-containing oils with monounsaturated fatty acid-containing oils, the effects of a catabolic illness or the effects of infection or risk of infection in an individual may be reduced. The oil included in the diet of the present invention typically comprises 45-85% $\omega 9$ monounsaturated fatty acids and comprises 5-75% of the total calories of the diet. The monounsaturated fatty acids preferably comprise 15-85% of the total fatty acids in the diet.

Preferred oils useful in treating stressed individuals are olive oil and canola oil which are rich in oleic acid. High oleic acid safflower or high oleic acid sunflower oils may also be used. Olive oil is primarily a mixture of mono-and-triglycerides, which are esters of glycerol with fatty acids. Olive oil also contains small quantities of free fatty acids, glycerol, phosphatides, pigments, carbohydrates, sterols and resinous substances. The major fatty acids present as glycerides in olive oil are oleic (18:1), linoleic (18:2), palmitoleic (16:1), palmitic (16:0), and stearic (18:0). The three principal fatty acids are typically present in the following ranges: oleic acid 56-83%, palmitic acid 7-20%, and linoleic acid 3-20%. Canola oil typically comprises 62-83% oleic acid and 10% $\omega 3$ fatty acids. High oleic acid safflower oils and high oleic acid sunflower oils can have 60-80% $\omega 9$ monounsaturated fatty acids and have primarily $\omega 6$ (e.g., linoleic) fatty acids as the remaining oils. The oils may be concentrated to provide a high percentage of monounsaturated fatty acids per unit volume.

The oils having $\omega 9$ monounsaturated fatty acids as the major fatty acid component can be administered to the individual enterally or parenterally. When the oil is administered parenterally, it is normally in the form of an emulsion of 1-40% lipid in water. The emulsion can be combined with other nutrients to provide a final concentration of monounsaturated fatty acid of 1-30%.

The invention also features a dietary supplement, preferably for parenteral use, having 10 to 90% by weight of an oil having an $\omega 9$ monounsaturated fatty acid as the major fatty acid component, 1-2% by weight of an emulsifier and sterile water. Higher levels (25-75%) of the monounsaturated fat are preferred. Emulsifiers useful in the supplement include egg yolk phospholipids and soybean phospholipids. The dietary supplement may also include 1-3% of an osmolality modifier such as glycerin. Such dietary supplements can be administered to an individual to minimize the effects of a catabolic illness in the individual or minimize the effects of infection or subsequent infection in an individual at risk of infection.

The following non-limiting examples will show the efficacy of the present invention.

EXAMPLE 1

This Example illustrates that animals fed a diet in which the primary lipid sources are oils rich in $\omega 9$ monounsaturated fatty acids rather than a diet containing oils rich in $\omega 6$ fatty acids minimizes the effects of endotoxin shock upon challenge with endotoxin. The following fats were used in this study: fish or menhaden oil (FI), an oil rich in $\omega 3$ fatty acids; safflower oil (SA), an oil rich in $\omega 6$ fatty acids; black currant seed oil (BC), an oil rich in $\omega 6$ fatty acids (linoleic plus gamma linolenic acid); medium chain triglycerides (MCT), primarily saturated $C_8$ and $C_{10}$ fatty acids; and olive oil, an oil rich in $\omega 9$ monounsaturated fatty acids. To compare the specific effects of each lipid to modulate the response to endotoxin shock, male Sprague Dawley rats (300 grams) were fed either one of the above fats in a semipurified diet or standard chow (CH) for 7 weeks.

At the end of the feeding period, venous catheters were placed for continuous endotoxin administration for 8 hours (3 mg/kg/hr). The endotoxin was a lipopolysaccharide derived from *E. coli* (Difco Laboratories). Arterial catheters were also inserted for hemodynamic monitoring and blood gas sampling. Resting energy expenditure (REE) was calculated by indirect calorimetry at 0, 2, 4, 6 and 8 hours. REE was calculated from oxygen consumption and $CO_2$ production using the Weir equation.

The diets are standard rat chow and semipurified diets such that the fat source is controlled and specific to that dietary group. The oil content is raised in the semipurified diets (except the standard rat chow) so the diet contains 13 percent by weight of lipid as opposed to the normal 5.5 percent. This allows 27 percent of the dietary calories to be lipid-derived as compared with the standard 14 percent. All the diets were equicaloric, except for the standard chow which contained less fat and the MCT diet which contains slightly less calories per gram.

The results demonstrate that animals fed olive oil developed the least acidosis as manifested by two factors: pH at Hour 7 (pH 7.49; $p<0.04$) and serum $HCO_3$ at Hour 8 (16mEq/l; $p<0.008$). Since acidosis often accompanies protein catabolism, reducing acidosis should correlate with lower levels of protein catabolism. In contrast, animals fed black currant seed oil, standard chow or MCT, each demonstrated a pH at Hour 7 of 7.45, the fish oil diet had a pH of 7.47, and the safflower diet had a pH of 7.46. In addition, serum $HCO_3$ at Hour 8 in animals fed black currant seed oil or MCT was 13 mEq/l while the values for fish oil, safflower oil and standard chow were 15, 14 and 15 mEq/l, respectively. This result also indicates reduced catabolism by diet modification.

Another important finding was in the resting energy expenditure (REE). Maintenance of the REE shows minimalizing of protein catabolism and better host response to the catabolic insult. REE was best preserved in the group of animals fed olive oil (Hour 6, 125 Kcal/kg/hr olive oil vs. 108 Kcal/kg/hr for standard chow, $p<0.03$). Accordingly, the olive oil diet provided significant advantages in treating endotoxin shock.

EXAMPLE 2

This Example illustrates one procedure for forming a dietary supplement for minimizing the effects of a catabolic illness in an individual or for enhancing resistance to infection.

The dietary supplement is preferably in the form of an oil emulsion. For each liter of emulsion, 50-400 grams of refined and bleached oil rich in ω9 monounsaturated fatty acids is mixed with about 11 grams of an emulsifier, e.g., egg yolk phospholipids USP, 22.5 grams of an osmolality modifier, e.g., glycerin USP, and sterile water USP to bring the volume to a liter. Specifically, the oil is added to a high shear mixer such as a Waring mixer with steel blades operated at 1,600 RPM. The phospholipids are added slowly to the oil and mixed at high speed for 6 minutes. Eight hundred milliliters of sterile water is added in a steady stream to the phospholipid and oil mixture and emulsified for 20 minutes at 1600 RPM. The attainment of the oil-in-water emulsion is confirmed by the "drop dispersion test." Emulsification is continued until the coarse oil emulsion disperses freely in water but not in oil.

The coarse emulsion is then passed through a high speed homogenizer five times until particle size is less than 1 micron. At that time, five more passes through the high speed homogenizer are performed and with each pass, glycerin is added to the emulsion. During the last five passes, additional water is added to make the final emulsion volume up to the one liter batch. Normally, all volumes are multiplied ten-fold and a ten liter batch is mixed at once.

Aliquots of the emulsion are set aside for measuring particle size which should be between 0.24 and 0.75 microns. The solutions are then passed through a five micron particle filter into sterile and pyrogen free evacuated containers. The emulsion is then sterilized at low temperature (105° C.) for 25 minutes. The solutions are cooled to room temperature and stored in the dark at 9° C. for one week. Prior to patient administration, the samples are retested for particle size and the presence of bacterial or endotoxin contamination. If the particle size is greater than 1 micron or the endotoxin concentration is greater than 1 ng, the batch of emulsion is discarded.

While the method and dietary supplement disclosed herein will not necessarily prevent catabolism in an individual or prevent the onset of infection, it will minimize the effects of a catabolic illness and promote survival of infected patients. The specific method and dietary supplement set forth herein are illustrative and those skilled in the art may determine other modifications and variations of these procedures. Such other modifications and variations are included within the scope of the following claims.

What is claimed is:

1. A method of minimizing the effects of a catabolic illness in an individual, comprising administering to the individual a diet which is controlled in the type of fatty acid intake, said diet including as the primary lipid source an oil having a ω9 monounsaturated fatty acid as the major fatty acid component.

2. The method of claim 1 wherein said monounsaturated fatty acid is oleic acid.

3. The method of claim 1 wherein said oil is selected from a group consisting of olive oil, canola oil and high oleic acid safflower or high oleic acid sunflower oil.

4. The method of claim 1 wherein said oil comprises 45-85% ω9 monounsaturated fatty acid.

5. The method of claim 1 wherein said monounsaturated fatty acid comprises 15-85% of the total fatty acids in the diet.

6. The method of claim 1 wherein said oil comprises 5-75% of the total calories of the diet administered to the individual.

7. The method of claim 4 wherein said oil is administered enterally.

8. The method of claim 5 wherein said fatty acids are administered enterally.

9. The method of claim 1 wherein said oil is administered parenterally as an emulsion of 1-40% lipid in water.

10. A method of minimizing the effects of an infection in an individual and minimizing the effects of subsequent infection in an individual at risk of infection, comprising administering to the individual a diet which is controlled in the type of fatty acid intake, said diet including as the primary lipid source an oil having a ω9 monounsaturated fatty acid as the major fatty acid component.

11. The method of claim 10 wherein said monounsaturated fatty acid is oleic acid.

12. The method of claim 10 wherein said oil is selected from a group consisting of olive oil, canola oil and high oleic acid safflower or high oleic acid sunflower oil.

13. The method of claim 10 wherein said oil comprises 45-85% monounsaturated fatty acid.

14. The method of claim 10 wherein said monounsaturated fatty acid comprises 15-85% of the total fatty acids in the diet.

15. The method of claim 10 wherein said oil comprises 5-75% of the total calories of the diet administered to the individual.

16. The method of claim 14 wherein said oil is administered enterally.

17. The method of claim 15 wherein said fatty acids are administered enterally.

18. The method of claim 10 wherein said oil is administered parenterally as an emulsion of 1-40% lipid in water.

19. The method of claim 10 wherein said patients are infected with infections selected from a group consisting of wound infections, empyemas, bacteremias, abscesses, and septicemias.

20. The method of claim 10 wherein said infections are caused by infectious agents selected from a group consisting of bacteria, viruses, parasites, and fungi.

21. The method of claim 10 wherein said individuals are at risk of infection at time of administration of the diet.

22. The method of claim 21 wherein said individuals at risk of infection are selected from a group consisting of individuals with secondary immunosuppression due to chemotherapy or diabetes mellitus, protein-malnourished individuals, and individuals undergoing surgery.

23. A method of minimizing the effects of a catabolic illness in an individual, comprising administering to the individual a dietary supplement including at least 5-40% by weight of an oil having an $\omega 9$ monounsaturated fatty acid as the major fatty acid component;

1-2% by weight emulsifier; and sterile water.

24. A method of minimizing the effects of an infection in an individual and minimizing the effects of subsequent infection in an individual at risk of infection, comprising administering to the individual a dietary supplement including at least 5-40% by weight of an oil having an $\omega 9$ monounsaturated fatty acid as the major fatty acid component;

1-2% by weight emulsifier; and sterile water.

* * * * *